United States Patent
Plouy

(10) Patent No.: US 9,795,102 B2
(45) Date of Patent: Oct. 24, 2017

(54) PEA VARIETY SV0371QF

(71) Applicant: Seminis Vegetable Seeds, Inc., St. Louis, MO (US)

(72) Inventor: Alexis J. Plouy, Twin Falls, ID (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 15/097,268

(22) Filed: Apr. 12, 2016

(65) Prior Publication Data

US 2017/0258027 A1     Sep. 14, 2017

Related U.S. Application Data

(60) Provisional application No. 62/305,894, filed on Mar. 9, 2016.

(51) Int. Cl.
*A01H 5/10*   (2006.01)
*A01H 1/02*   (2006.01)
*C12N 15/82*   (2006.01)
*A01G 1/00*   (2006.01)

(52) U.S. Cl.
CPC ............... *A01H 5/10* (2013.01); *A01G 1/001* (2013.01); *A01H 1/02* (2013.01); *C12N 15/8241* (2013.01)

(58) Field of Classification Search
None
See application file for complete search history.

(56) References Cited

U.S. PATENT DOCUMENTS

| | | | |
|---|---|---|---|
| 7,714,194 B2 | 5/2010 | Plouy | |
| 7,714,195 B2 | 5/2010 | Plouy | |
| 7,906,708 B2 | 3/2011 | Webster | |
| 8,039,691 B2 | 10/2011 | Plouy | |
| 8,053,640 B2 | 11/2011 | Plouy | |
| 8,076,538 B2 | 12/2011 | Plouy | |
| 8,269,067 B2 | 9/2012 | Webster | |
| 8,378,175 B2 * | 2/2013 | Plouy | A01H 5/10 435/410 |
| 8,471,104 B2 | 6/2013 | Plouy | |
| 8,629,327 B2 | 1/2014 | Plouy | |
| 9,029,640 B2 | 5/2015 | Webster | |
| 9,167,780 B2 | 10/2015 | Plouy | |
| 9,173,349 B2 | 11/2015 | Plouy | |
| 9,258,963 B2 | 2/2016 | Plouy | |
| 9,357,726 B2 | 6/2016 | Plouy | |
| 9,374,960 B2 | 6/2016 | Plouy | |
| 2006/0206968 A1 | 9/2006 | Webster | |
| 2010/0017903 A1 | 1/2010 | Webster | |

FOREIGN PATENT DOCUMENTS

EP      2 465 342      6/2012

OTHER PUBLICATIONS

Li et al (1994, Cereal Chem. 71(1):87-90).*
U.S. Appl. No. 15/094,811, filed Apr. 8, 2016, Kmiecik.
U.S. Appl. No. 15/094,815, filed Apr. 8, 2016, Plouy.
U.S. Appl. No. 15/094,818, filed Apr. 8, 2016, Plouy.
Moose SP, Mumm RH., "Molecular plant breeding as the foundation for 21st century crop improvement", Plant Physiol.; 147(3):969-77; Jul. 2008.
Variety specific information as indicated in transmittal letter of Sep. 22, 2016 Information Disclosure Statement for U.S. Appl. No. 15/097,268.

* cited by examiner

*Primary Examiner* — Stuart F Baum
(74) *Attorney, Agent, or Firm* — Dentons US LLP; Alissa Eagle Esq.

(57) ABSTRACT

The invention provides seed and plants of the pea line designated SV0371QF. The invention thus relates to the plants, seeds and tissue cultures of pea line SV0371QF, and to methods for producing a pea plant produced by crossing a plant of pea line SV0371QF with itself or with another pea plant, such as a plant of another line. The invention further relates to seeds and plants produced by such crossing. The invention further relates to parts of a plant of pea line SV0371QF, including the seed, pod, and gametes of such plants.

24 Claims, No Drawings

PEA VARIETY SV0371QF

CROSS-REFERENCE TO RELATED APPLICATIONS

This application claims the priority of U.S. Provisional Appl. Ser. No. 62/305,894, filed Mar. 9, 2016, the entire disclosure of which is incorporated herein by reference.

FIELD OF THE INVENTION

The present invention relates to the field of plant breeding and, more specifically, to the development of pea line SV0371QF.

BACKGROUND OF THE INVENTION

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit or pod properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

Pea plants are able to reproduce by self-fertilization and cross-fertilization. Thus far, however, commercial pea varieties have been inbred lines prepared through self fertilization (Kevin McPhee, In: Journal of New Seeds: Innovations in production, biotechnology, quality, and marketing; ISSN: 1522-886X, 6:2/3, 2005).

Peas are one of the top vegetables used for processing in the United States; with approximately 90% of the grown pea acreage used for processed consumption (NASS Census of Agriculture 2002). The pea is an annual cool season plant, growing best in slightly acidic soil. Many cultivars reach maturity about 60 days after planting. Pea plants can have both low-growing and vining cultivars. The vining cultivars grow thin tendrils from the leaves of the plant, which coil around available supports. The pea pods form at the leaf axils of the plant.

As with other legumes, pea plants are able to obtain fixed nitrogen compounds from symbiotic soil bacteria. Pea plants therefore have a substantially reduced fertilizer requirement compared to non-leguminous crops. This advantage adds to their commercial value, particularly in view of increasing fertilizer costs, and has generated considerable interest in the creation of new pea plant cultivars.

SUMMARY OF THE INVENTION

In one aspect, the present invention provides a pea plant of the line designated SV0371QF. Also provided are pea plants having all the physiological and morphological characteristics of the pea line designated SV0371QF. Parts of the pea plant of the present invention are also provided, for example, including pollen, an ovule, a seed, a pod, and a cell of the plant.

The invention also concerns the seed of pea line SV0371QF. In one embodiment, pea seed of the invention may be provided as an essentially homogeneous population of pea seed of the line designated SV0371QF. Essentially homogeneous populations of seed are generally free from substantial numbers of other seed. Therefore, seed of line SV0371QF may be defined as forming at least about 97% of the total seed, including at least about 98%, 99% or more of the seed. The population of pea seed may be particularly defined as being essentially free from hybrid seed. The seed population may be separately grown to provide an essentially homogeneous population of pea plants designated SV0371QF.

In another aspect of the invention, a plant of pea line SV0371QF comprising an added heritable trait is provided. The heritable trait may comprise a genetic locus that is, for example, a dominant or recessive allele. In one embodiment of the invention, a plant of pea line SV0371QF is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a pea plant of line SV0371QF is provided. The tissue culture will preferably be capable of regenerating pea plants capable of expressing all of the physiological and morphological characteristics of the line, and of regenerating plants having substantially the same genotype as other plants of the line. Examples of some of the physiological and morphological characteristics of the line SV0371QF include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides pea plants regenerated from a tissue culture of the invention, the plants having all the physiological and morphological characteristics of line SV0371QF.

In yet another aspect of the invention, processes are provided for producing pea seeds, pods and plants, which processes generally comprise crossing a first parent pea plant with a second parent pea plant, wherein at least one of the first or second parent pea plants is a plant of the line designated SV0371QF. These processes may be further exemplified as processes for preparing hybrid pea seed or plants, wherein a first pea plant is crossed with a second pea plant of a different, distinct line to provide a hybrid that has, as one of its parents, the pea plant line SV0371QF. In these processes, crossing will result in the production of seed. The seed production occurs regardless of whether the seed is collected or not.

In one embodiment of the invention, the first step in "crossing" comprises planting seeds of a first and second parent pea plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent pea plants into plants that bear flowers. A third step may comprise preventing self-pollination of the plants, such as by emasculating the male portions of flowers, (i.e., treating or manipulating the flowers to produce an emasculated parent pea plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent pea plants. Yet another step comprises harvesting the seeds from at least one of the parent pea plants. The harvested seed can be grown to produce a pea plant or hybrid pea plant.

The present invention also provides the pea seeds and plants produced by a process that comprises crossing a first parent pea plant with a second parent pea plant, wherein at least one of the first or second parent pea plants is a plant of the line designated SV0371QF. In one embodiment of the invention, pea seed and plants produced by the process are first generation ($F_1$) hybrid pea seed and plants produced by crossing a plant in accordance with the invention with another, distinct plant. The present invention further contemplates plant parts of such an $F_1$ hybrid pea plant, and methods of use thereof. Therefore, certain exemplary embodiments of the invention provide an $F_1$ hybrid pea plant and seed thereof.

In still yet another aspect, the present invention provides a method of producing a plant derived from line SV0371QF, the method comprising the steps of: (a) preparing a progeny plant derived from line SV0371QF, wherein said preparing comprises crossing a plant of the line SV0371QF with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line SV0371QF. The plant derived from line SV0371QF may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line SV0371QF is obtained which possesses some of the desirable traits of the line as well as potentially other selected traits.

In certain embodiments, the present invention provides a method of producing peas comprising: (a) obtaining a plant of pea line SV0371QF, wherein the plant has been cultivated to maturity, and (b) collecting peas from the plant.

In still yet another aspect of the invention, the genetic complement of the pea plant line designated SV0371QF is provided. The phrase "genetic complement" is used to refer to the aggregate of nucleotide sequences, the expression of which sequences defines the phenotype of, in the present case, a pea plant, or a cell or tissue of that plant. A genetic complement thus represents the genetic makeup of a cell, tissue or plant, and a hybrid genetic complement represents the genetic make up of a hybrid cell, tissue or plant. The invention thus provides pea plant cells that have a genetic complement in accordance with the pea plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line SV0371QF could be identified by any of the many well known techniques such as, for example, Simple Sequence Length Polymorphisms (SSLPs) (Williams et al., *Nucleic Acids Res.,* 1 8:6531 6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

In still yet another aspect, the present invention provides hybrid genetic complements, as represented by pea plant cells, tissues, plants, and seeds, formed by the combination of a haploid genetic complement of a pea plant of the invention with a haploid genetic complement of a second pea plant, preferably, another, distinct pea plant. In another aspect, the present invention provides a pea plant regenerated from a tissue culture that comprises a hybrid genetic complement of this invention.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of pea line SV0371QF. This line shows uniformity and stability within the limits of environmental influence for the traits described hereinafter. Pea line SV0371QF provides sufficient seed yield. By crossing with a distinct second plant, uniform F1 hybrid progeny can be obtained. The development of pea line SV0371QF can be summarized as follows.

Pea line SV0371QF, also known as "13-C7-DLF-1035" is a full-season maturing intermediate sieve dark green pea with an afila foliage. It was selected based on productivity and disease resistance: SV0371QF caries the Fw1 and Fw2 alleles for resistance to race 1 and 2 of the wilt fungus, *Fusarium oxysporum* fsp *pisi*, the En allele for resistance to Pea Enation Mosaic Virus (PEMV), and the recessive er1 allele for powdery mildew resistance. In addition, it shows an improved behavior to the pea root rot complex. Its unique characteristic is the combination of these diseases resistances. The most similar variety is believed to be Estancia from *Seminis* which differs in its susceptibility to Powdery Mildew and Enation virus.

A. Origin and Breeding History of Pea Line SV0371QF

Pea line SV0371QF (DLFC709-1035) is a mid-season intermediate sieve dark green determinate afila variety that was developed by pedigree selection. The cross that led to the development was made between a SEMINIS line of complex parentage: F319XF234xNvII and the SEMINIS variety Estancia as a pollen parent.

As is true with other garden pea varieties, a small percentage of off-types can occur within commercially acceptable limits for almost any characteristic during the course of repeated multiplications. No variants are known or expected to occur.

B. Physiological and Morphological Characteristics of Pea Line SV0371QF

In accordance with one aspect of the present invention, there is provided a plant having the physiological and morphological characteristics of pea line SV0371QF. A description of the physiological and morphological characteristics of pea line SV0371QF is presented in Table 1.

TABLE 1

Physiological and Morphological Characteristics of Line SV0371QF

| CHARACTERISTIC | SV0371QF | Comparison Variety - Estancia/ Subito |
|---|---|---|
| 1. Type | Garden | Garden |
| 2. Maturity | | |
| node number of first bloom | 13-14 | 13-14 |
| number of days earlier than the comparison variety | 0 | |
| number of days later than the comparison variety | 0 | |
| 3. Plant | | |
| height (in centimeters) | 53.6 cm | 57.3 cm |
| number of centimeters shorter than the comparison variety | 4.2 cm | |
| anthocyanin coloration | absent | absent |
| stem: type of anthocyanin coloration of axil | absent | absent |
| stem: fasciation | absent | absent |
| stem: number of nodes up to and including first fertile node (main stem only; measurement should include the first 2 nodes with "scale" leaves) | medium | |
| 4. Vine | | |
| habit | indeterminate | indeterminate |
| branching | 1-2 branches | 1-2 branches |
| internodes | zig zag | zig zag |
| number of nodes | 19.8 | 19.9 |
| stockiness | heavy | heavy |
| foliage: color | blue-green | blue-green |
| foliage: intensity of color (only varieties with foliage color: green) | dark | |
| leaf: leaflets | absent | absent |
| 5. Leaflets | | |
| leaflet type | semi | semi |
| 6. Stipules | | |
| present or lacking? | present | present |
| clasping or not clasping? | clasping | clasping |
| marbled or not marbled? | marbled | marbled |
| color | blue green | blue green |
| RHS Color Chart number for color of stipules | N137A | N137A |
| size | medium | |
| stipule: width | medium | medium |
| stipule: length from axil to tip | medium | medium |
| stipule: length of lobe below axil | medium | |
| stipule: flecking | present | present |
| stipule: density of flecking (assessment should be made on the main stem only; presence of flecking on any stipule on the main stem means that flecking is present; the density of flecking should be observed on the part of the plant with the most flecking) | medium | |
| petiole: length from axil to first leaflet or tendril (A-B) | long | long |
| petiole: length from axil to last tendril (A-C) (only varieties with leaflets absent) | medium | medium |

TABLE 1-continued

Physiological and Morphological Characteristics of Line SV0371QF

| CHARACTERISTIC | SV0371QF | Comparison Variety - Estancia/Subito |
|---|---|---|
| time of flowering (when 30% of plants have at least one flower open) | late | late |
| plant: maximum number of flowers per node (only varieties with stem fasciation absent) | three | |
| 7. Flower Color | | |
| venation | greenish | greenish |
| standard | white | white |
| color of standard (only varieties with plant anthocyanin coloration absent) | white | white |
| wing | white | white |
| keel | white | white |
| flower: shape of base of standard | moderately arched | level |
| flower: undulation of standard | absent or very weak | weak |
| flower: shape of apex of upper sepal [refer to diagram] | accuminate | accuminate |
| peduncle: length of spur (length of C-D) | short | short |
| peduncle: length from stem to first pod (length of A-B) | medium | medium |
| peduncle: length between first and second pods (length of B-C) | medium | long |
| 8. Pods | | |
| shape | slightly curved | slightly curved |
| end | blunt | blunt |
| color | medium green | dark green |
| pod: color | green | green |
| pod: intensity of green color (only varieties with pod color green) | medium | |
| surface (smooth or rough?) | smooth | smooth |
| surface (shiny or dull?) | dull | dull |
| borne | double & triple | double |
| length | 7.0 cm | 7.6 cm |
| width (between sutures) | 11.8 mm | 12.1 mm |
| pod: maximum width | medium | medium |
| pod: parchment | entire | entire |
| excluding varieties with pod parchment: entire: thickened wall | absent | absent |
| varieties with pod: thickened wall absent: shape of distal part | blunt | pointed |
| pod: number of ovules | medium | medium |
| number of seeds per pod | 8.9 | 8.5 |
| immature seed: intensity of green color | dark | dark |
| 9. Seeds | | |
| color (95-100 Tenderometer) | green | green |
| shape (dry-mature) | angular | angular |
| surface (dry-mature) | wrinkled | wrinkled |
| luster (dry-mature) | dull | dull |
| color pattern (dry-mature) | monocolor | monocolor |
| primary color (dry-mature) | cream & green | cream & green |
| hilum color (dry-mature) | white | white |
| cotyledon color (dry-mature) | green | green |
| number of grams per 100 seeds | 17.7 g | 15.8 g |
| seed: weight | medium | |
| seed: shape | rhomboid (irregularly compressed on radicle and distal surfaces; also irregularly compressed on abaxial surfaces) | rhomboid |
| seed: type of starch grains | compound | |
| seed: wrinkling of cotyledon (Only varieties with seed shape: cylindrical: and type of starch grains: simple) | present | present |
| seed: color of cotyledon | green | green |
| seed: marbling of testa (only varieties with plant anthocyanin coloration present) | absent | absent |
| seed: violet or pink spots on testa (only varieties with plant anthocyanin coloration present) | absent | absent |
| seed: hilum color | same color as testa | same color as testa |

*These are typical values. Values may vary due to environment. Other values that are substantially equivalent are within the scope of the invention.

C. Breeding Pea Line SV0371QF

One aspect of the current invention concerns methods for crossing the pea line SV0371QF with itself or a second plant and the seeds and plants produced by such methods. These methods can be used for propagation of line SV0371QF, or can be used to produce hybrid pea seeds and the plants grown therefrom. Hybrid seeds are produced by crossing line SV0371QF with second pea parent line.

The development of new varieties using one or more starting varieties is well known in the art. In accordance with the invention, novel varieties may be created by crossing line SV0371QF followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line SV0371QF and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with SV0371QF for the purpose of developing novel pea lines, it will typically be preferred to choose those plants which either themselves exhibit one or more selected desirable characteristics or which exhibit the desired characteristic(s) when in hybrid combination. Examples of potentially desirable traits include, but are not necessarily limited to, improved resistance to viral, fungal, and bacterial pathogens, improved insect resistance, pod morphology, herbicide tolerance, environmental tolerance (e.g. tolerance to temperature, drought, and soil conditions, such as acidity, alkalinity, and salinity), growth characteristics, nutritional content, taste, and texture. Improved taste and texture applies not only to the peas themselves, but also to the pods of those varieties yielding edible pods. In peas, as in other legumes, taste and nutritional content are particularly affected by the sucrose and starch content.

Among fungal diseases of particular concern in peas are *Ascochyla pisi, Cladosporium pisicola* (leaf spot or scab), *Erysiphe polygoni* (powdery mildew), *Fusarium oxysporum* (wilt), *Fusarium solani* (*Fusarium* root rot), *Mycosphaerella pinodes* (Mycosphaerella blight), *Peronospora viciae* (downy mildew), *Phythium* sp. (pre emergence damping-off), *Botrytis cinerea* (grey mold), *Aphanomyces euteiches* (common root rot), *Thielaviopsis basicola* (black root rot), and *Sclerotina sclerotiorum* (*sclerotina* white mold). Pea plant viral diseases include: Bean yellow mosaic virus (BYMV), Bean leaf roll virus (BLRV), Pea Early Browning Virus (PEBV), Pea Enation Mosaic virus (PEMV), Pea Mosaic Virus (PMV), Pea seed-borne Mosaic virus (PSbMV) and Pea Streak Virus (PSV). An important bacterial disease affecting pea plants is caused by *Pseudomonas pisi* (bacterial blight), (Muehlbauer et al., In: Description and culture of dry peas, *USAD-ARS Agricultural Reviews and Manuals*, Western Region, California, 37:92, 1983; Davies et al., In: Pea (*Pisum sativum* L.), Summerfield and Roberts (Eds.), Williams Collins Sons and Co. Ltd, UK, 147-198, 1985; van Emden et al., In: Pest, disease and weed problems in pea lentil *faba* bean and chickpea. p., Summerfield (Ed.), Kluwer Academic Publishers, Dordrecht, The Netherlands, 519-534, 1988).

Insect pests that may be of particular concern in peas include *Aphis cracivora* (Groundnut aphid), *Acyrthosiphon pisum* (Pea aphid), *Kakothrips robustus* (Pea thrips), *Bruchis pisorum* (Pea seed beetle), *Callosobruchus chinensis* (Adzuki bean seed beetle), *Apion* sp. (Seed weevil), *Sitona lineatus* (Bean weevil), *Contarina pisi* (Pea midge), *Helicoverpa armigera* (African bollworm), *Diachrysia obliqua* (Pod borer), *Agriotis* sp. (Cut worms), *Cydia nigricana* (Pea moth), *Phytomuza horticola* (Leaf minor), *Heliothis Zea* (American bollworm), *Etiella Zinckenella* (Lima bean pod borer), *Ophiomyia phaseoli* (Bean fly), *Delia platura* (Bean seed fly), *Tetranychus* sp. (Spider mites), *Pratylenchus penetrants* (Root lesion nematodes), *Ditylenchus dipsaci* (Stem nematode), *Heterodera goettingiana* (Pea cyst nematode), and *Meloidogyne javanica* (Root knot nematode), (van Emden et al., In: Pest, disease and weed problems in pea lentil *faba* bean and chickpea. p., Summerfield (Ed.), Kluwer Academic Publishers, Dordrecht, The Netherlands, 519-534, 1988; Muehlbauer et al., In: Description and culture of dry peas, *USAD-ARS Agricultural Reviews and Manuals*, Western Region, California, 37:92, 1983).

D. Performance Characteristics

Performance characteristics of the line SV0371QF were the subject of an objective analysis of the performance traits of the line relative to other lines. The results of the analysis are presented below.

TABLE 2

Performance Characteristics For Pea Line SV037QF

| Variety | Nber Years | SubM | Sub SubM | Seeds | Fol | HU | Days From Sow. | Mat | Yield (qx/ha) | % Yield | TdrTV | <7.5 | 7.5-8.2 |
|---|---|---|---|---|---|---|---|---|---|---|---|---|---|
| SV0371QF | 4 | G | FS | wr | A | 779 | 85 | 9 | 75.9 | 88% | 100 | 13% | 19% |
| DLF-C7091035 | 20091900 | G | FS | rPM-R2-EN-BYMV.af.mdncgr | A A | 797 | 86 | 9 | 86.9 | 91% | 120 | 7% | 12% |
| SOLUTION | 4 | G | FS1 | wr | A | 743 | 84 | 7 | 801 | 127% | 100 | 6% | 11% |
| SOLUTION | 1900 | G | FS1 | wr | A | 762 | 86 | 7 | 86.9 | 117% | 120 | 3% | 6% |
| MINOTAUR | 4 | G | FS2 | wr | A | 763 | 84 | 8 | 85.9 | 97% | 100 | 7% | 12% |
| MINOTAUR | 2009 | G | FS2 | wr | A | 780 | 86 | 8 | 99.0 | 101% | 120 | 4% | 7% |
| BINGO | 4 | G | FS1 | wr | A | 777 | 84 | 9 | 79.0 | 92% | 100 | 3% | 6% |
| BINGO | 2009 | G | FS1 | wr | A | 793 | 86 | 8 | 86.7 | 91% | 120 | 1% | 3% |
| RAVENNA | 4 | G | FS2 | wr | Afa | 786 | 86 | 9 | 86.8 | 106% | 100 | 2% | 5% |
| RAVENNA | 2008 | G | FS2 | wr | Afa | 812 | 87 | 9 | 94.4 | 103% | 120 | 1% | 3% |
| BOOGIE | 4 | G | FS | wr | A | 784 | 85 | 9 | 97.3 | 113% | 100 | 2% | 3% |
| BOOGIE | 2009 | G | FS | wr | A | 803 | 87 | 9 | 108.5 | 113% | 120 | 1% | 2% |
| GALLANT | 4 | G | FS2 | wr | A | 787 | 85 | 10 | 76.8 | 87% | 100 | 7% | 11% |
| GALLANT | 2009 | G | FS2 | wr | A | 808 | 87 | 9 | 85.1 | 87% | 120 | 4% | 6% |
| ZELDA | 4 | G | FS2 | wr | A | 784 | 85 | 10 | 86.8 | 99% | 100 | 5% | 8% |
| ZELDA | 2009 900 | G | FS2 | wr | A | 808 | 87 | 10 | 94.0 | 98% | 120 | 3% | 5% |

TABLE 2-continued

Performance Characteristics For Pea Line SV037QF

| | | | | | | | | | | | | | |
|---|---|---|---|---|---|---|---|---|---|---|---|---|---|
| SPANDIMO | 4 | G | FS | wr | Afa | 777 | 81 | 10 | 89.1 | 110% | 100 | 3% | 5% |
| SPANDIMO | 2009 | G | FS | wr | FA | 808 | 83 | 10 | 99.7 | 112% | 120 | 2% | 3% |
| SERGE | 4 | G | L | wr | A | 834 | 79 | 12 | 73.9 | 108% | 100 | 4% | 8% |
| SERGE | 1009 190 | G | L | wr | A | 853 | 80 | 11 | 84.2 | 109% | 120 | 2% | 5% |
| PERSEPHONE | 4 | G | FS2 | wr | A | 813 | 87 | 12 | 100.2 | 116% | 100 | 10% | 20% |
| PERSEPHONE | 20091900 | G | FS2 | wr | A | 833 | 89 | 11 | 106.8 | 111% | 120 | 6% | 12% |
| SUBITO = ESTANCIA | 4 | DLW | FS2 | wr | A | 780 | 81 | 9 | 78.5 | 92% | 100 | 6% | 13% |
| SUBITO = ESTANCIA | 2006 | DLW | FS2 | wr | A | 806 | 83 | 9 | 89.6 | 95% | 120 | 4% | 7% |

| Variety | SF | 8.2-8.75 | 8.75-9.3 | 9.3-10.2 | >10.2 | SS | Field Rat. | Thresh | Col. Fresh | Col. Hom. | Col.af.Blanch | AIS | Tdr at AIS 12% |
|---|---|---|---|---|---|---|---|---|---|---|---|---|---|
| SV0371QF | 31% | 28% | 27% | 10% | 3% | 3.13 | | 9% | 2.7 | | 3.0 | 13.8 | 82 |
| DLF-CT091035 | 20% | 25% | 34% | 17% | 4% | 3.53 | | 9% | 2.7 | | 3.0 | 15.8 | 82 |
| SOLUTION | 17% | 22% | 29% | 23% | 10% | 3.83 | | 3% | 3.1 | | 4.0 | 13.7 | 85 |
| SOLUTION | 9% | 15% | 30% | 31% | 15% | 4.25 | | 3% | 3.1 | | 4.0 | 16.1 | 85 |
| MINOTAUR | 18% | 21% | 27% | 23% | 11% | 3.80 | | 3% | 2.0 | | 2.3 | 12.9 | 92 |
| MINOTAUR | 10% | 14% | 27% | 31% | 18% | 4.27 | | 3% | 2.0 | | 2.3 | 15.2 | 92 |
| BINGO | 8% | 11% | 21% | 33% | 27% | 4.57 | | 5% | 2.8 | | 4.7 | 13.4 | 85 |
| BINGO | 5% | 6% | 16% | 36% | 37% | 4.93 | | 5% | 2.8 | | 4.7 | 15.3 | 85 |
| RAVENNA | 7% | 11% | 27% | 33% | 21% | 4.50 | | 4% | 2.2 | | 3.6 | 13.7 | 84 |
| RAVENNA | 4% | 6% | 21% | 40% | 30% | 4.85 | | 4% | 2.2 | | 3.6 | 15.9 | 84 |
| BOOGIE | 5% | 7% | 18% | 37% | 32% | 4.82 | | 5% | 2.9 | | 3.3 | 14.8 | 79 |
| BOOGIE | 2% | 3% | 11% | 38% | 45% | 5.19 | | 5% | 2.9 | | 3.3 | 17.5 | 79 |
| GALLANT | 18% | 17% | 25% | 26% | 14% | 3.95 | | 7% | 3.4 | | 3.0 | 13.4 | 88 |
| GALLANT | 10% | 13% | 24% | 33% | 20% | 4.37 | | 7% | 3.4 | | 3.0 | 15.7 | 88 |
| ZELDA | 13% | 16% | 24% | 30% | 17% | 4.19 | | 4% | 2.9 | | 1.3 | 13.4 | 88 |
| ZELDA | 8% | 10% | 21% | 35% | 26% | 4.58 | | 4% | 2.9 | | 1.3 | 15.8 | 88 |
| SPANDIMO | 8% | 11% | 25% | 36% | 20% | 4.45 | | 7% | 1.6 | | 3.2 | 13.4 | 75 |
| SPANDIMO | 5% | 6% | 17% | 39% | 32% | 4.87 | | 7% | 1.6 | | 3.2 | 15.3 | 15 |
| SERGE | 12% | 13% | 24% | 33% | 18% | 4.27 | | 7% | 3.1 | | 4.3 | 16.1 | 21 |
| SERGE | 7% | 10% | 22% | 38% | 23% | 4.58 | | 7% | 3.1 | | 4.3 | 18.0 | 21 |
| PERSEPHONE | 30% | 25% | 24% | 15% | 5% | 3.31 | | 9% | 1.4 | | 2.3 | 13.1 | 91 |
| PERSEPHONE | 18% | 21% | 29% | 23% | 9% | 3.77 | | 9% | 1.4 | | 2.3 | 15.5 | 91 |
| SUBITO = ESTANCIA | 19% | 27% | 26% | 22% | 6% | 3.62 | | 4% | 3.5 | | 2.9 | 13.6 | 85 |
| SUBITO = ESTANCIA | 11% | 19% | 30% | 31% | 9% | 4.05 | | 4% | 3.5 | | 2.9 | 15.6 | 85 |

Nber Years = Number of years of field trials from which data was collected and pooled.;
Fol = type of foliage (A = Afila, Afa = Afila faciated)
HU = Heat Units to harvest;
Mat = Maturity in days at harvest compared to the reference variety SPRING.
Yield (qx/ha): in quintals (100 kg), quantity of fresh peas harvested on one Hectare;
TdrTV = Tenderometer value at harvest;
<7.5 to >10.2 = in mm, the percentage of berries with the mentioned caliber;
AV SS = coefficient calculated from the amount of peas per caliber;
Thresh: percentage of non full pods in the total harvest;
Col. Fresh = Fresh color of the berries;
Col.af.Blanch = Color of the berries after blanching;
AIS = percentage of Alcohol Insoluble Solids in the berries at the given Tenderometer value;
Tdr at AIS 12%: Tenderometer value at which you should harvest the peas in order to have an AIS % of 12.

E. Further Embodiments of the Invention

In certain aspects, the invention provides plants modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those pea plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental pea plant which contributes the locus for the desired characteristic is termed the nonrecurrent or donor parent. This terminology refers to the fact that the nonrecurrent parent is used one time in the backcross protocol and therefore does not recur. The parental pea plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a pea plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny pea plants of a backcross in which SV0371QF is the recurrent parent comprise (i) the desired trait from the non-recurrent parent and (ii) all of the physiological and morphological characteristics of pea line SV0371QF as determined at the 5% significance level when grown in the same environmental conditions.

Pea varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the downy mildew resistance trait. For this selection process, the progeny of the initial cross are sprayed with downy mildew spores prior to the backcrossing. The spraying eliminates any plants which do not have the desired downy mildew resistance characteristic, and only those plants which have the downy mildew resistance gene are used in the subsequent backcross. This process is then repeated for all additional backcross generations.

Selection of pea plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of pea are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., *Nucleic Acids Res.,* 1 8:6531 6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

F. Plants Derived from Pea Line SV0371QF by Genetic Engineering

Many useful traits that can be introduced by backcrossing, as well as directly into a plant, can also be introduced by genetic transformation techniques. Genetic transformation may therefore be used to insert a selected transgene into the pea line of the invention or may, alternatively, be used for the preparation of transgenes which can be introduced by backcrossing. Methods for the transformation of plants, including pea plants, are well known to those of skill in the art (see, e.g., Schroeder et al., *Plant Physiol.* 101(3): 751-757, 1993). Techniques which may be employed for the genetic transformation of pea plants include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

Microprojectile bombardment techniques are widely applicable, and may be used to transform virtually any plant species. An illustrative embodiment of a method for delivering DNA into plant cells by bombardment is the Biolistics Particle Delivery System, which can be used to propel particles coated with DNA or cells through a screen, such as a stainless steel or Nytex screen, onto a surface covered with target pea cells. The screen disperses the particles so that they are not delivered to the recipient cells in large aggregates.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio-Technology*, 3(7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio/Technology*, 3:629-635, 1985; U.S. Pat. No. 5,563,055). *Agrobacterium*-mediated transformation is a particularly beneficial method for producing recombinant pea-plants. Transformed pea plants may be obtained by incubating pea explant material with *Agrobacterium* containing the DNA sequence of interest (U.S. Pat. No. 5,286,635; U.S. Pat. No. 5,773,693).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994), and Ellul et al. (*Theor. Appl. Genet.*, 107: 462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for pea plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S) the nopaline synthase promoter (An et al., *Plant Physiol.*, 88:547, 1988), the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO J.*, 4:2723, 1985), (3) hormones, such as abscisic acid (Marcotte et al., *Plant Cell*, 1:969, 1989), (4) wounding (e.g., wun1, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989).

Exemplary nucleic acids which may be introduced to the pea lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a pea plant according to the invention. Non-limiting examples of particular genes and corresponding phenotypes one may choose to introduce into a pea plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Royal Horticultural Society (RHS) color chart value: The RHS color chart is a standardized reference which allows accurate identification of any color. A color's designation on the chart describes its hue, brightness and saturation. A color is precisely named by the RHS color chart by identifying the group name, sheet number and letter, e.g., Yellow-Orange Group 19A or Red Group 41B.

Self-pollination: The transfer of pollen from the anther to the stigma of the same plant.

Single Locus Converted (Conversion) Plant: Plants which are developed by a plant breeding technique called backcrossing wherein essentially all of the morphological and physiological characteristics of an inbred are recovered in addition to the characteristics conferred by the single locus transferred into the inbred via the backcrossing technique. By "essentially all," it is meant that all of the characteristics of a plant are recovered that are otherwise present when compared in the same environment and save for the converted locus, other than an occasional variant trait that might arise during backcrossing or direct introduction of a transgene. A single locus may comprise one gene, or in the case of transgenic plants, one or more transgenes integrated into the host genome at a single site (locus).

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a pea plant by transformation.

H. Deposit Information

A deposit of pea line SV0371QF, disclosed above and recited in the claims, has been made with the American Type Culture Collection (ATCC), 10801 University Blvd., Manassas, Va. 20110-2209. The date of deposit was Mar. 14, 2016. The accession number for those deposited seeds of pea line SV0371QF is ATCC Accession No. PTA-122918. Upon issuance of a patent, all restrictions upon the deposit will be removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A seed of pea line SV0371QF, a sample of seed of said line having been deposited under ATCC Accession Number PTA-122918.

2. A plant of pea line SV0371QF, a sample of seed of said line having been deposited under ATCC Accession Number PTA-122918.

3. A plant part of the plant of claim 2.

4. The plant part of claim 3, wherein said part is selected from the group consisting of a pod, pollen, an ovule and a cell.

5. A pea plant, or a plant part thereof, having all of the physiological and morphological characteristics of the pea plant of claim 2.

6. A tissue culture of regenerable cells of pea line SV0371QF, a sample of seed of said line having been deposited under ATCC Accession Number PTA-122918.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A pea plant regenerated from the tissue culture of claim 6, wherein the regenerated plant expresses all of the physiological and morphological characteristics of pea line SV0371QF, a sample of seed of said line having been deposited under ATCC Accession Number PTA-122918.

9. A method of producing seed, the method comprising crossing the plant of claim 2 with itself or a second plant.

10. The method of claim 9, wherein the plant of pea line SV0371QF is the female parent.

11. The method of claim 9, wherein the plant of pea line SV0371QF is the male parent.

12. An $F_1$ hybrid seed produced by the method of claim 9.

13. An $F_1$ hybrid plant produced by growing the seed of claim 12.

14. A method for producing a seed of a line SV0371QF-derived pea plant, the method comprising the steps of:
(a) crossing a pea plant of line SV0371QF with a second pea plant, a sample of seed of said line having been deposited under ATCC Accession Number PTA-122918; and
(b) allowing seed of a SV0371QF-derived pea plant to form.

15. The method of claim 14, further comprising the steps of:
(c) crossing a plant grown from said SV0371QF-derived pea seed with itself or a second pea plant to yield additional SV0371QF-derived pea seed;
(d) growing said additional SV0371QF-derived pea seed of step (c) to yield additional SV0371QF-derived pea plants; and
(e) repeating the crossing and growing steps of (c) and (d) to generate further SV0371QF-derived pea plants.

16. A method of vegetatively propagating a plant of pea line SV0371QF, the method comprising the steps of:
(a) collecting tissue capable of being propagated from a plant of pea line SV0371QF, a sample of seed of said line having been deposited under ATCC Accession Number PTA-122918;
(b) cultivating said tissue to obtain proliferated shoots; and
(c) rooting said proliferated shoots to obtain rooted plantlets.

17. The method of claim 16, further comprising growing plants from said rooted plantlets.

18. A method of introducing a desired trait into pea line SV0371QF, the method comprising:
(a) crossing a plant of line SV0371QF with a second pea plant that comprises a desired trait to produce $F_1$ progeny, a sample of seed of said line SV0371QF having been deposited under ATCC Accession Number PTA-122918;
(b) selecting an $F_1$ progeny that comprises the desired trait;
(c) crossing the selected $F_1$ progeny with a plant of line SV0371QF to produce backcross progeny;
(d) selecting backcross progeny comprising the desired trait and the physiological and morphological characteristic of pea line SV0371QF; and
(e) repeating steps (c) and (d) three or more times to produce selected fourth or higher backcross progeny that comprise the desired trait and essentially all of the physiological and morphological characteristics of pea line SV0371QF when grown in the same environmental conditions.

19. A pea plant produced by the method of claim 18.

20. A seed that produces the plant of claim 19.

21. A method of producing a plant of pea line SV0371QF comprising an added desired trait, the method comprising introducing a transgene conferring the desired trait into a plant of pea line SV0371QF, a sample of seed of said line SV0371QF having been deposited under ATCC Accession Number PTA-122918.

22. A pea plant produced by the method of claim 21.

23. A seed that produces the plant of claim 22.

24. A method of producing peas, the method comprising:
(a) obtaining the plant of claim 2, wherein the plant has been cultivated to maturity, and
(b) collecting peas from the plant.

* * * * *